United States Patent
McConnell et al.

(10) Patent No.: US 11,998,558 B2
(45) Date of Patent: *Jun. 4, 2024

(54) SYNTHETIC COMPOSITION FOR TREATING ANTIBIOTIC ASSOCIATED COMPLICATIONS

(71) Applicant: GLYCOM A/S, Hørsholm (DK)

(72) Inventors: Bruce McConnell, La Tour de Peilz (CH); Louise Kristine Vigsnæs, Copenhagen NV (DK); David Paul Kronlage, Slidell, LA (US)

(73) Assignee: GLYCOM A/S, Hørsholm (DK)

( * ) Notice: Subject to any disclaimer, the term of this patent is extended or adjusted under 35 U.S.C. 154(b) by 5 days.

This patent is subject to a terminal disclaimer.

(21) Appl. No.: 17/120,881

(22) Filed: Dec. 14, 2020

(65) Prior Publication Data

US 2021/0100822 A1  Apr. 8, 2021

Related U.S. Application Data

(63) Continuation of application No. 15/776,654, filed as application No. PCT/DK2016/050371 on Nov. 17, 2016, now Pat. No. 10,864,224.

(60) Provisional application No. 62/256,170, filed on Nov. 17, 2015, provisional application No. 62/299,186, filed on Feb. 24, 2016, provisional application No. 62/345,959, filed on Jun. 6, 2016.

(51) Int. Cl.
*A61K 31/702* (2006.01)
*A23L 33/125* (2016.01)
*A61P 31/04* (2006.01)

(52) U.S. Cl.
CPC .......... *A61K 31/702* (2013.01); *A23L 33/125* (2016.08); *A61P 31/04* (2018.01); *A23V 2002/00* (2013.01); *Y02A 50/30* (2018.01)

(58) Field of Classification Search
CPC . A23L 33/125; A61K 2300/00; A61K 31/702; A61P 31/04
See application file for complete search history.

(56) References Cited

U.S. PATENT DOCUMENTS

| 8,197,872 B2 | 6/2012 | Mills et al. |
| 10,864,224 B2 * | 12/2020 | McConnell ............. A61P 31/04 |
| 2012/0171165 A1 * | 7/2012 | Buck ...................... A61P 25/00 514/23 |

FOREIGN PATENT DOCUMENTS

| EP | 2388010 A1 | 11/2011 |
| EP | 2522232 A1 | 11/2012 |
| EP | 2589302 A1 | 5/2013 |
| WO | 2009047537 A1 | 4/2009 |
| WO | 2012092160 | 7/2012 |
| WO | 2012158517 A1 | 11/2012 |
| WO | 2013032674 A1 | 3/2013 |
| WO | 2015071131 A1 | 5/2015 |
| WO | 2015095747 A1 | 6/2015 |
| WO | 2015157098 A1 | 10/2015 |

OTHER PUBLICATIONS

"Statement on the safety of lacto-N-neotetraose and 2'-0-fucosyllactose as novel food ingredients in food supplements for children," EFSA Panel on Dietetic Products, Nutrition and Allergies (NDA), EFSA Journal, 2015, vol. 13(11):4299, 12 pages.
Rivero-Urgell, M. et al. "Oligosaccharides: application in infant food", Early Human Development (2001) vol. 65(Suppl.), abstract.
Bannerjee, T., et al., "Prebiotics: A New Hope Against Antibiotic Associated Diarrhea," Anti-Infective Agents, 2014, vol. 12, pp. 139-144.
Barbut, F., et al., "Managing antibiotic associated diarrhoea," British Medical Journal, 2002, vol. 342, pp. 1345-1346.
Newburg, D.S., et al., "Human Milk Glycans Protect Infants Against Enteric Pathogens," Annu. Rev. Nutr., 2005, vol. 25, pp. 37-58.

\* cited by examiner

*Primary Examiner* — Pancham Bakshi
(74) *Attorney, Agent, or Firm* — Neal, Gerber & Eisenberg LLP

(57) ABSTRACT

The invention relates to a synthetic composition comprising human milk oligosaccharides for use in at least partially restoring the commensal gastrointestinal microbiota and preventing or mitigating antibiotic associated diarrhoea.

10 Claims, No Drawings

SYNTHETIC COMPOSITION FOR TREATING ANTIBIOTIC ASSOCIATED COMPLICATIONS

CROSS-REFERENCE TO RELATED APPLICATION

This application is a continuation application of U.S. application Ser. No. 15/776,654, filed on May 16, 2018, which is a national stage entry pursuant to 35 U.S.C. § 371 of International Application No. PCT/DK2016/050371, filed on Nov. 17, 2016, which claims priority to U.S. Provisional Application No. 62/256,170, filed on Nov. 17, 2015, U.S. Provisional Application No. 62/299,186, filed on Feb. 24, 2016, and U.S. Provisional Application No. 62/345,959, filed on Jun. 6, 2016, the contents of all of which are fully incorporated herein by reference.

FIELD OF THE INVENTION

This invention relates to a method and composition for the prophylaxis or treatment of adverse effects associated with an antibiotic treatment, for example the prophylaxis or treatment of C. difficile infection.

BACKGROUND OF THE INVENTION

The human intestine harbours an estimated $10^{13}$ to $10^{14}$ bacterial cells, and the number of bacteria outnumbers the total number of cells in the body by a factor of 10 (Gill et al, Science 312, 1355 (2006)). The microbiota of the human intestine is a complex and very dynamic microbial ecosystem, which is considered to serve numerous important functions for its human host, including protection against pathogens, induction of immune regulatory functions, nutrient processing and metabolic functions (Tojo et al, *World J. Gastroenterol.* 20, 15163 (2014)).

Recent research has been able to link imbalances in the intestinal microbiota to both intestinal and extra-intestinal diseases (Guinane et al, *Ther. Adv. Gastroenterol.* 6, 295 (2013)). Antibiotics, especially broad spectrum antibiotics, dramatically impact the microbiota and its balance and have been implicated in the pathogenesis of many health conditions. Given the extensive use of antibiotics, this has a large health and health economic impact. For example, an analysis of U.S. antibiotic prescription rates in 2010 demonstrated widespread antibiotic use in children (Hicks et al, *New Engl. J. Med.* 368, 1461 (2013)). An average child in the USA has received nearly three antibiotic courses by the age of 2 years, about ten courses by the age of 10 years, and about 17 courses by the age of 20 years.

A common detrimental impact of the overuse of antibiotics is the development of antibiotic resistance of pathogenic bacteria. However, the detrimental impact which antibiotics inflict on the intestinal microbial populations by contributing to intestinal dysbiosis could be a more significant concern. Diarrhoea is one of the most significant short-term, dysbiosis-related adverse effects of antibiotic therapy. When it occurs in conjunction with antibiotic use, in the absence of any other cause, it is referred to as antibiotic-associated diarrhoea (AAD). The spectrum of AAD ranges from mild symptomatic loose stools to life-threatening colitis. The most commonly cited mechanism for AAD is intestinal overgrowth of pathogenic microorganisms, especially *Clostridium difficile, Escherichia coli, Clostridium perfringens, Salmonella, Staphylococcus aureus* and *Klebsiella* as a consequence of intestinal dysbiosis induced by antibiotics, especially penicillins, cephalosporins and clindamycin (Song et al, *Korean J. Intern. Med.* 23, 9 (2008)). As an example, *C. difficile* forms spores, which helps the bacterium to resist antibiotic treatment. In a dysbiotic intestine, the spores can germinate and *C. difficile* can colonize and grow. After colonization, *C. difficile* mediates its effect on disease development through two toxins, TcdA and TcdB. These toxins cause an increase in permeability and inflammation. Infection with *C. difficile* is an increasing challenge worldwide. The rate of hospitalization due to *C. difficile* has doubled from 2000 to 2005. The infection has proven difficult to manage, with relatively high mortality (estimated to be 1-25% in the US), and 15-35% of patients experience at least one recurrent *C. difficile* infection after end of treatment (Antharam et al, *J. Clin. Microb.* 51, 2884 (2013)).

However, not all AAD patients exhibit signs of pathogenic bacteria and other mechanisms are also believed to be involved. For example, various antibiotics (including ampicillin) can cause an imbalance in saccharolytic and proteolytic bacteria in the colon leading to reduced fermentation of indigestible carbohydrates. As a result, there is an increase in unfermented carbohydrates in the colon, leading to an osmotic diarrhoea. Additionally, because of the reduced saccharolytic activity, a deficiency in bacterial metabolites, such as the short chain fatty acids (SCFA) acetate, propionate and butyrate, has been observed. SCFA normally stimulate salt and water reabsorption in the colon, hence a lack of SCFAs can lead to profuse diarrhoea. Imbalance in the intestinal microbiota with antibiotics has also shown to increase intestinal permeability, reduce MUC2 production in goblet cells and thinning of the mucus layer, resulting in an impaired integrity of the mucosal barrier function.

Further, the intestinal microbiota does not necessarily recover from antibiotic treatment. In a human study with healthy adults consuming antibiotics for 5 days, total faecal bacterial concentrations as well as bifidobacteria concentrations were significantly reduced compared to before antibiotic therapy. Also, two months post exposure, resilience could not be observed for bifidobacteria, and for total bacteria, in most of the subjects (Mangin et al, *PLoS One* 7, e50257 (2012)). Another human study with healthy volunteers consuming antibiotics for 10 days revealed a large effect on the faecal microbial diversity and change in microbial composition which lasted for a year, with the most pronounced microbial shift after one month (Rashid et al, *Clin. Infect. Dis.* 60, S77 (2015)). Together, these results suggest that antibiotic therapy induces short-term and long-term alterations in the human intestinal microbiota (Jernberg et al. *Microbiology* 156, 3216 (2010)).

Apart from the shorter term side effects of antibiotic treatment, there are concerns that the impact on the intestinal microbiota has longer term health impacts. For example, the incidence of autoimmune and metabolic diseases has increased sharply in westernized countries over the past six decades. The rise in these conditions has prompted speculation that the advent of antibiotics in the 1940s, coupled with a rise in caesarean-section births, changes in dietary habits and urbanization, may have altered the human-associated microbiota to make individuals more susceptible to these diseases. Further, antibiotic-mediated changes to the intestinal microbiota have been associated with the development of asthma, eczema, atopic dermatitis and other allergic sensitization, autoimmune encephalitis, candidiasis, cholera and pathogen induced colitis. They are also believed to amplify diet induced obesity and effects on hepatic gene expression, metabolic hormone levels and visceral fat accumulation (Blaser, *Nature* 476, 393 (2011); Nobel et al, *Nat. Commun.* 6:7486 doi: 10.1038/ncomms8486 (2015)).

Hence, it would be advantageous to be able to prevent or reduce the damaging consequences of antibiotic treatment by reducing or preventing dysbiosis and restoring the intestinal microbiota, preferably by promoting a beneficial intestinal microbiota composition after antibiotic treatment. Further, it would be advantageous to prevent or reduce the negative effects of antibiotic treatment on gut barrier function and/or restore the gut barrier function after antibiotic treatment.

One approach which has been investigated is to minimise the negative consequences of antibiotic therapy by using probiotics. A review analysing sixteen studies, comprising 3,432 participants, indicated that probiotics had a protective effect with respect to preventing paediatric AAD (Johnston et al. *Cochrane Database Syst. Rev.* doi: 10.1002/14651858.CD004827.pub3 (2011)). However, the addition of a small number of different probiotics to the intestine is unlikely to fully restore and promote a beneficial intestinal microbiota composition after antibiotic treatment.

Another approach has been the use of prebiotics. Prebiotics have been defined as: "Selectively fermented ingredients that allow specific changes, both in the composition and/or activity in the gastrointestinal microbiota that confer benefits upon host well-being and health" (Gibson et al, *Nutr. Res. Rev.* 17, 259 (2004)). For example, a human study has shown that co-administration of 12 g of oligofructose per day during antibiotic therapy reduced the occurrence of relapses of successfully treated *C. difficile* associated diarrhoea to 8%, compared with 34% in controls (Lewis et al, *Aliment. Pharmacol. Ther.* 21, 469 (2005)), however the same amount of oligofructose failed to protect elderly subjects receiving broad-spectrum antibiotics from AAD (Lewis et al, *Clin. Gastroenterol. Hepatol.* 3, 442 (2005)).

WO 2010/065652 describes the use of human milk permeates to treat *C. difficile* related colitis, a common complication of prolonged broad-spectrum antibiotic treatment. However, using human milk is not commercially realistic as a general treatment option.

WO 2013/032674 describes the use of human milk oligosaccharides (HMOs) to treat gastro-intestinal injuries due to several causes, including antibiotic treatment.

There remains, however, a need for safe options for preventing or treating negative consequences of antibiotic therapy in humans, such as *C. difficile* infections, diarrhoea, dysbiosis, depletion of SCFAs and increase in the level of toxins produced by enterotoxigenic bacteria.

SUMMARY OF THE INVENTION

A first aspect of this invention relates to one or more HMOs selected from the group consisting of fucosylated HMOs and core HMOs, preferably a mixture of one or more fucosylated HMOs and one or more core HMOs, for use in:
the prophylaxis or treatment of antibiotic-associated diarrhoea in a human patient undergoing or having undergone antibiotic therapy,
the prophylaxis or treatment of dysbiosis of the lower gastrointestinal tract in a human patient undergoing or having undergone antibiotic therapy, in particular increasing the abundance of bifidobacteria and/or reducing the abundance of Proteobacteria and/or enterotoxigenic bacteria in said human patient, and/or
the prophylaxis or treatment of primary or recurrent *Clostridium difficile* infection in a human patient undergoing or having undergone antibiotic therapy,
wherein at least 2 g of one or more HMOs is administered to the human daily.

A second aspect of this invention is a synthetic composition, preferably in a unit dose form, for use in:
the prophylaxis or treatment of antibiotic-associated diarrhoea in a human patient undergoing or having undergone antibiotic therapy,
the prophylaxis or treatment of dysbiosis of the lower gastro-intestinal tract in a human patient undergoing or having undergone antibiotic therapy, in particular increasing the abundance of bifidobacteria and/or reducing the abundance of Proteobacteria and/or enterotoxigenic bacteria in said human, and/or
the prophylaxis or treatment of primary or recurrent *Clostridium difficile* infection in a human patient undergoing or having undergone antibiotic therapy,
the synthetic composition comprising at least 2 g of one or more HMOs selected from the group consisting of fucosylated HMOs and core HMOs, preferably of a mixture of one or more fucosylated HMOs and one or more core HMOs. Preferably, the composition is administered daily.

A third aspect of this invention is a method for the prophylaxis or treatment of antibiotic-associated diarrhoea in a human patient undergoing or having undergone antibiotic therapy, the method comprising administering daily to the patient at least 2 g of one or more HMOs selected from the group consisting of fucosylated HMOs and core HMOs, preferably of a mixture of one or more fucosylated HMOs and one or more core HMOs.

A fourth aspect of this invention is a method for reducing the amount of toxins produced by enterotoxigenic bacteria in the gastro-intestinal tract of a human patient undergoing or having undergone antibiotic therapy, the method comprising administering daily to the patient at least 2 g of one or more HMOs selected from the group consisting of fucosylated HMOs and core HMOs, preferably of a mixture of one or more fucosylated HMOs and one or more core HMOs. Preferably, the toxins reduced are selected from toxin A and toxin B of *Clostridium difficile* and toxins from *Clostridium perfringens, Staphylococcus aureus, Salmonella, Pseudomonas aeruginosa* and *Escherichia coli*.

A fifth aspect of this invention is a method for increasing the abundance of bifidobacteria, and/or reducing the abundance of Proteobacteria and/or enterotoxigenic bacteria, in a human patient undergoing or having undergone antibiotic therapy, the method comprising administering daily to the patient at least 2 g of one or more HMOs selected from the group consisting of fucosylated HMOs and core HMOs, preferably of a mixture of one or more fucosylated HMOs and one or more core HMOs. Preferably, the bifidobacteria is a *Bifidobacterium* of the *B. adolescentis* phylogenetic group, especially of *Bifidobacterium adolescentis* and/or *Bifidobacterium pseudocatenulatum*. Preferably, the Proteobacteria and/or enterotoxigenic bacteria are *Escherichia coli* and/or *Clostridium difficile*.

A sixth aspect of this invention is a method for reducing the long-term health risks associated with antibiotic treatment of a human patient, the method comprising administering daily to the patient at least 2 g of one or more HMOs selected from the group consisting of fucosylated HMOs and core HMOs, preferably of a mixture of one or more fucosylated HMOs and one or more core HMOs. Preferably, the risk of autoimmune and metabolic diseases later in life is reduced.

A seventh aspect of this invention is a method for primary prevention of *Clostridium difficile* infection in a human patient undergoing or having undergone antibiotic therapy, the method comprising administering daily to the patient an effective amount of one or more HMOs selected from the group consisting of fucosylated HMOs and core HMOs, preferably of a mixture of one or more fucosylated HMOs and one or more core HMOs. Preferably, the efficient amount of one or more HMOs is at least 2 grams.

An eighth aspect of this invention is a method for the prophylaxis or treatment of recurrent *Clostridium difficile* infection in a human patient undergoing or having undergone antibiotic therapy, the method comprising administering daily to the patient an effective amount of one or more HMOs selected from the group consisting of fucosylated HMOs and core HMOs, preferably of a mixture of one or more fucosylated HMOs and one or more core HMOs. Preferably the occurrence of *Clostridium difficile* relapse is prevented. Preferably, the efficient amount of one or more HMOs is at least 2 grams.

A ninth aspect of this invention is a method for the stimulation of production of short-chain fatty acids (SCFA) in a human patient undergoing or having undergone antibiotic therapy, the method comprising administering daily to the patient at least 2 g of one or more HMOs selected from the group consisting of fucosylated HMOs and core HMOs, preferably of a mixture of one or more fucosylated HMOs and one or more core HMOs. Preferably, the SCFA is acetate, propionate and/or butyrate.

In accordance with the third to ninth aspects of the invention, the patient is preferably administered one or more HMOs in neat form (i.e. undiluted) or diluted with water prior to administration, or in the form of a synthetic composition, more preferably in one or more unit dosage forms, even more preferably in a single unit dosage form.

In accordance with the third to ninth aspects of the invention, the patient is preferably administered one or more HMOs for at least 14 days after termination of the patient's antibiotic therapy. More preferably, the patient is administered a synthetic composition comprising about 2 g to about 10 g, particularly about 3.5 g to about 7.5 g, per day, of one or more HMOs selected from the group consisting of fucosylated HMOs and core HMOs, preferably of a mixture of one or more fucosylated HMOs and one or more core HMOs. The patient may be administered an initial, higher treatment dose of about 5 g to 10 g/day for a period of up to about 30 days, for example about 14 days. Thereafter the patient may be administered a lower, maintenance dose of about 2 g to 5 g/day. The maintenance dose may be administered chronically over an extended period.

In accordance with the first to ninth aspects of the invention, the one or more HMOs selected from the group consisting of fucosylated HMOs and core HMOs is preferably two or more HMOs. In one embodiment, the two or more HMOs selected from the group consisting of fucosylated HMOs and core HMOs is a mixture comprising or consisting of a fucosylated HMO and a core HMO. Particularly, the mixture contains or consists of a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and FpLNnH-II, and a core HMO selected from the list consisting of LNT, LNnT, LNH, LNnH, pLNH and pLNnH. In one preferred embodiment, the mixture contains or consists of a fucosylated HMO selected from the list consisting of 2'-FL, 3-FL and DFL, and a core HMO selected from the list consisting of LNT and LNnT. In some preferred embodiments the mixture comprises or consists of 2'-FL and LNnT.

Also, the mixture or the synthetic composition preferably contains more fucosylated HMOs than core HMOs (by weight), for example about 1.5:1 to about 5:1 of 2'-FL: LNnT, more preferably about 2:1 to 4:1. Moreover, the synthetic composition can contain a source of glutamine, threonine, cysteine, serine, proline or a combination of two or more of these amino acids. The synthetic composition can contain a probiotic bacteria which is able to metabolise HMOs, for example a bifidobacteria.

Also in accordance with the first to ninth aspects of the invention, the human patient preferably is a child, preferably of age between 3 to 10 years, or an elderly patient of aged over 60 years.

DETAILED DESCRIPTION OF THE INVENTION

In accordance with this invention, the following terms preferably have the following meanings:

"Human milk oligosaccharide" or "HMO" means a complex carbohydrate found in human breast milk (Urashima et al.: *Milk Oligosaccharides*, Nova Biomedical Books, New York, 2011, *Chen Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated (core HMOs).

"Core human milk oligosaccharide" or "core HMO" means an HMO, the core structure of which is not substituted by an α L-fucopyranosyl and/or an α-N-acetyl-neuraminyl (sialyl) moiety. Examples of core HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH).

"Fucosylated human milk oligosaccharide" or "fucosylated core HMO" means an HMO, the core structure of which is substituted by an α L-fucopyranosyl moiety. Examples of fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyl-lactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (FpLNnH-II) and fucosyl-lacto-N-neohexaose (FLNnH). "*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:54 (2014)).

"Microbiota", "microflora" and "microbiome" mean a community of living microorganisms that typically inhabits a bodily organ or part, particularly the gastro-intestinal organs of non-infant humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Proteobacteria" are a phylum of Gram-negative bacteria and include a wide variety of pathogenic bacteria, such as *Escherichia, Salmonella, Vibrio, Helicobacter, Yersinia* and many other notable genera.

"Enterotoxigenic bacteria" means bacteria producing enterotoxins. An enterotoxin is a protein exotoxin released by a microorganism that targets the intestines, such as exotoxins produced by following bacteria *V. cholerae*, enterotoxigenic *E. coli* (ETEC), some strains of *S. aureus, V. parahaemolyticus, Y. enterocolitica, Aeromonas* species and *C. perfringens*.

"Dysbiosis of the lower gastrointestinal tract" means a condition in the gastrointestinal tract associated with an impaired microbiota, where normally dominating bacterial species are underrepresented or outcompeted by abnormal or pathogenic species.

"Patient" means a human of 3 years of age or older, that is a child, a teenager, an adult or an elderly, who is diagnosed with a disease. In one preferred embodiment, a patient is an elderly of 60 years of age or older.

"Prophylaxis" means treatment given or action taken to prevent the onset of a disease or a pathological condition, including reducing risks or threats to health. Non-limiting examples of pathological conditions include diarrhoea, decreased amount of short chain fatty acids or increased amount of enterotoxins in the gastro-intestinal tract, gastrointestinal tract dysbiosis, etc.

"Primary infection" refers to the first time a host, e.g. human patient is exposed to a pathogen, e.g. pathogenic bacteria, and infected by this pathogen, i.e. the pathogen has completed a resting or dormant period in the host. "Recurrent infection" in the present context is a second, third, fourth etc. infection by the same or similar pathogen in a certain period of time after the primary infection was cured.

"Therapy" means treatment given or action taken to reduce or eliminate symptoms of a disease or pathological condition.

"Lower gastro-intestinal tract" in the present context includes the jejunum and ileum of the small intestine and the large intestine. "Enteral administration" means any conventional form for delivery of a composition that causes the deposition of the composition in the gastrointestinal tract (including the stomach). Methods of enteral administration include feeding through a naso-gastric tube or jujenum tube, oral, sublingual and rectal.

"Oral administration" means any conventional form for the delivery of a composition through the mouth. Accordingly, oral administration is a form of enteral administration.

"Effective amount" means an amount of a composition that provides an HMO in a sufficient amount to render a desired treatment outcome. An effective amount can be administered in one or more doses to achieve the desired treatment outcome.

"Broad spectrum antibiotic" means an antibiotic that acts against a wide range of disease-causing bacteria including both Gram-positive and Gram-negative bacteria. Examples of broad spectrum antibiotics are Vancomycin, Ampicillin, Amoxicillin, Amoxicillin/clavulanic acid, Carbapenems, Piperacillin/tazobactam, Levofloxacin, Gatifloxacin, Moxifloxacin, Ciprofloxacin, Streptomycin, Tetracycline, Chloramphenicol, Ticarcillin.

"Long-term health risk associated with antibiotic treatment" means a physiological condition or disease that develops and is diagnosed in a patient who had previously received an antibiotic as a part of therapeutic or another treatment and has stopped this treatment before the first occurrence of said physiological condition or disease in the patient. Examples of long-term health risks associated with antibiotic treatment include but not limited to autoimmune or metabolic diseases, diarrhoea, ulcerative colitis, impaired immune function, obesity, food absorption, depression, sepsis, asthma, allergies.

The term "later in life" refers to effects first observed and/or measured in a patient after a certain period of time following termination of antibiotic treatment of this patient, i.e. after a period of time during which the patient did not take an antibiotic as a part of a therapeutic or another treatment, such as 1-3 months following after the termination of the antibiotic treatment, such as after 3-6 months, or 6-12 month, or 1-2 years, or 2-5 years, or 5-10 years, or even more than 10 years, following after the termination of the antibiotic treatment.

In accordance with this invention, it has been discovered that administration of at least 2 g per day of one or more HMOs selected from the group consisting of fucosylated HMOs and core HMOs, preferably of a mixture of one or more core HMOs and one or more fucosylated HMOs, to a human patient who is receiving or has received antibiotic treatment:

at least partially restores the commensal gastrointestinal microbiota of the patient and, in particular, increases the abundance of bifidobacteria and/or reduces the abundance of Proteobacteria and/or enterotoxigenic bacteria in the patient's gastrointestinal tract, and/or increases the production of SCFA, especially acetate, propionate and/or butyrate, in the patient's colon, and/or decreases the production of enterotoxins, and/or prevents or mitigates antibiotic associated diarrhoea in the patient.

A single HMO or a mixture of HMOs may be selected from the group consisting of fucosylated HMOs and core HMOs described herein.

This treatment can partially avoid or even prevent the consequences of antibiotic therapy. Such consequences can involve profound changes to the patient's intestinal microbiota which does not necessarily return to a healthy state once the antibiotic therapy is completed. The resulting dysbiosis can adversely affect the patient's health. Modulating the microbiota in the gastrointestinal tract of the patient to specifically increase bifidobacteria can prevent or at least treat the dysbiosis, restore SCFA levels and reduce enterotoxigenic bacteria and their toxins. In particular, the increase in abundance of bifidobacteria, for example *Bifidobacterium adolescentis*, can reduce the adherence of enterotoxigenic bacteria such as *Clostridium difficile, Clostridium perfringens, Staphylococcus aureus, Salmonella, Pseudomonas aeruginosa* and *Escherichia coli* to intestinal epithelial cells. The enterotoxigenic bacteria may be antibiotic resistant. This treatment can also improve the patient's gut barrier function. Further the treatment can also reduce the risks of developing *Clostridium difficile* infection in a human patient undergoing or having undergone antibiotic therapy, and/or occurrence of relapse in a human patient undergoing or having undergone antibiotic therapy to treat *Clostridium difficile* infection.

The fucosylated HMOs and core HMOs can be isolated by well-known processes from milk(s) secreted by mammals including, but not limited to human, bovine, ovine, porcine, or caprine species. These HMOs can also be produced by well-known processes using microbial fermentation, enzymatic processes, chemical synthesis, or combinations of these technologies. As examples, using chemistry, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979 and mixtures of HMOs can be made as described in WO 2012/113405. As examples of enzymatic production, fucosylated HMOs can be made as described in WO 2012/127410, and advantageously diversified blends of HMOs can be made as described in WO 2012/156897 and WO 2012/156898. With regard to biotechnological methods, WO 01/04341, WO 2007/101862, WO 2015/032412 and WO 2015/032413 describe how to make core and fucosylated HMOs using genetically modified *E. coli*.

The fucosylated HMO(s) and core HMO(s) are administered, preferably as a mixture, in a synthetic composition which can take any appropriate form. The term "synthetic composition" designates a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. For example, the composition can be in the form of a nutritional composition which contains other macronutrients such as proteins, lipids or other carbohydrates, or micronutrients. The synthetic composition can also be in unit dosage forms such as supplements and pharmaceutical compositions.

Nutritional Compositions

The synthetic composition, containing one or more HMOs selected from the group consisting of fucosylated HMOs and core HMOs, preferably a mixture of one or more core HMOs and one or more fucosylated HMOs, can be a nutritional composition. It can contain sources of one or more proteins, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed gastrointestinal tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline or a combination of two or more of these amino acids. The glutamine source can be L-glutamine, a glutamine dipeptide and/or a glutamine enriched protein. Glutamine can be included due to the use of glutamine by enterocytes as an energy source. Threonine, serine and proline are important amino acids for the production of mucin. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 µg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 μg/ml, for example about 0.034 μg/ml to about 5 μg/ml of beta-carotene.

The nutritional composition preferably also contains reduced concentrations of sodium; for example from about 300 mg/I to about 400 mg/I. The remaining electrolytes can be present in concentrations set to meet needs without providing an undue renal solute burden on kidney function. For example, potassium is preferably present in a range of about 1180 to about 1300 mg/I; and chloride is preferably present in a range of about 680 to about 800 mg/I.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HNO19, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-13), colorants, flavours, and stabilisers, lubricants, and so forth. The probiotic preferably includes a *Bifidobacterium*.

The nutritional composition can be in the form of a soluble powder, a liquid concentrate, or a ready-to-use formulation. The composition can be fed to a patient via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.2% to about 4.0%, including from about 0.4% to about 3%, including from about 0.8% to about 2.0%. When the nutritional product is a concentrated nutritional liquid, the total concentration of HMOs in the liquid, by weight of the liquid, is from about 0.4% to about 8.0%, including from about 0.8% to about 6.0%, including from about 1.6% to about 4.0%. When in solid form for reconstitution in liquid, the amount of HMO in the solid will depend upon the recommended reconstitution level. Preferably, a dose of 2 g of HMO is delivered in no more than about 1 litre of reconstituted liquid, more preferably about 250 ml of reconstituted liquid.

Unit Dosage Forms

Preferably, the synthetic composition, containing one or more HMOs selected from the group consisting of fucosylated HMOs and core HMOs, preferably a mixture of one or more core HMOs and one or more fucosylated HMOs, is in a unit dosage form such as a capsule, tablet or sachet. In each unit dose, the synthetic composition contains about 2 g to about 10 g, preferably about 3.5 g to about 7.5 g, of one or more HMOs selected from the group consisting of fucosylated HMOs and core HMOs, preferably a mixture of fucosylated and core HMOs.

The unit dosage form can also contain nutritionally or pharmaceutically acceptable carriers, diluents, excipients, lubricants, colorants, binders, and disintegrants. Suitable carriers, diluents, excipients, lubricants, colorants, binders, and disintegrants include phosphate buffered saline solution, mixtures of ethanol in water, water and emulsions such as an oil/water or water/oil emulsion, polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. The unit dosage form can also include suitable antioxidants such as vitamin A, carotenoids, vitamin C, vitamin E, selenium, flavonoids, polyphenols, lycopene, lutein, lignan, coenzyme Q10 ("CoQIO") and glutathione.

The unit dosage form can also include therapeutic agents such as antiviral agents, antibiotics, probiotics, analgesics, and anti-inflammatory agents.

The unit dosage form, especially those in sachet form, can also include various macronutrients or micronutrients. For example glutamine, threonine, cysteine, serine, proline or a combination of two or more of these amino acids, can be included.

The unit dosage form can be made to be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered forms can include binders, lubricants, inert diluents, flavouring agents, and humectants. Orally administered forms such as tablets can optionally be coated and can be formulated so as to provide sustained, delayed or controlled release of HMOs.

The unit dosage form can also be made to be administered by rectal suppository, aerosol tube, naso-gastric tube or direct infusion into the gastrointestinal tract or stomach.

Administration

The amount of one or more HMOs selected from the group consisting of fucosylated HMOs and core HMOs, preferably a mixture of one or more fucosylated HMOs and one or more core HMOs required to be administered in the synthetic composition to a patient will vary depending upon factors such as the patient's age, the weight, the diet, and other medications being administered. However, the required amount can be readily set by a medical practitioner and would generally be in the range from about 2 g to about 20 g per day, in certain embodiments from about 3 g to about 15 g per day, from about 4 g to about 10 g per day, in certain embodiments from about 5 g to about 10 g per day, in certain embodiments from about 6 g to about 7.5 g per day. An appropriate dose can be determined based on several factors, including, for example, age, body weight, other ailments and/or diseases, the incidence and/or severity of side effects and the manner of administration. Appropriate dose ranges may be determined by methods known to those skilled in the art. During an initial treatment phase, the dosing can be higher (for example 3 g to 20 g per day, preferably 3 g to 15 g per day, more preferably 5 g to 10 g per day, in certain embodiments 6 g to 7.5 g per day). During a maintenance phase, the dosing can be reduced (for example, 2 g to 10 g per day, preferably 3 g mg to 7.5 g per day, more preferably 3 g to 5 g per day).

Whilst the invention has been described with reference to a preferred embodiment, it will be appreciated that various modifications are possible within the scope of the invention.

EXAMPLES

Example 1

A total of 100 male and female healthy adults are recruited to participate in the study. After a screening visit and run-in period of 1-2 weeks, the participants are selected and randomized into ten groups, each of 10 subjects. One group is administered daily a placebo product containing 2 grams of glucose. The remaining 9 groups are administered daily a treatment product containing one of the following: a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 2 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 2 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each participant has an exit visit with the medical team. Faecal samples and blood samples are collected.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached. These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

To assess the *Bifidobacterium* community, ITS profiling of DNA samples is performed according to Milani et al, *FEMS Microbiol. Ecol.* 90, 493 (2014). Table 1 below shows the percentage increase of *Bifidobacterium* species with high sequence similarity to *B. adolescentis* compared to that of other *Bifidobacterium* species identified in human faeces after consumption of HMOs as determined from faecal analyses. Additionally, the result from the profiling of the *Bifidobacterium* community shows that mainly the abundance of *B. adolescentis* increases when consuming a single HMO, whereas mainly the abundance of *B. pseudocatenulatum* increases when consuming a mix of two HMOs. Both *B. adolescentis* and *B. pseudocatenulatum* are members of the *B. adolescentis* phylogenetic group. It can be seen that oral ingestion of the HMOs clearly increases the abundance of *B. adolescentis* and/or *B. pseudocatenulatum* in the microbiota of healthy adults, as well as its relative abundance compared to the totality of other *Bifidobacterium* species.

TABLE 1

|  | B. adolescentis phylogenetic group | totality of B. longum + B. bifidum + B. animalis lactis + B. angulatum |
| --- | --- | --- |
| 20 g LNnT | 185 | 105 |
| 10 g LNnT | 195 | 130 |
| 5 g LNnT | 90 | 50 |
| 20 g 2'-FL | 120 | 15 |
| 10 g 2'-FL | 325 | 20 |
| 5 g 2'-FL | 50 | 0 |
| 20 g mix | 320 | 265 |
| 10 g mix | 190 | 165 |
| 5 g mix | 25 | 20 |
| Placebo | 15 | −5 |

The abundance of Proteobacteria is reduced in all groups as compared to placebo.

Example 2

A total of 40 children of age 5 to 10 years are recruited to participate in the study. The children are commencing a broad spectrum, antibiotic therapy prescribed by a doctor for an infectious disorder. All recruited children and their caretakers are able and willing to understand and comply with the study procedures. Children are excluded if: they have participated in a clinical study one month prior to screening visit; they are suffering from a severe disease such as gastro-intestinal diseases, malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study, and consumed on a regular basis any medication that might interfere with symptom evaluation 2 weeks prior to the study.

At a screening visit, medical history and concomitant medication is registered. Additionally, eligibility criteria are checked and eligible subjects are randomised into two groups, each of 20 children. The treatment period (6 weeks) is divided into two, as follows:

Period 1 (2 weeks): Group 1 (placebo), Group 2 (treatment product).

Period 2 (4 weeks): Group 1 (placebo), Group 2 (treatment product).

The treatment product contains 5 grams of a combination of 2'-FL and LNnT (2:1 mass ratio), while the placebo product contains 5 grams of glucose. Both products are in powder form in a sachet. The products are each administered daily as a bolus at breakfast, and diet is not controlled; however, the participants are asked not to change their normal diet over the course of the study.

At the initial visit, faecal sample kits and either treatment or placebo products are distributed. Each child's caretaker is instructed to keep the faecal samples in the freezer until the next visit. The children and caretaker are reminded not to change the children's usual diet during the study. A faecal sample is collected at this visit and stored at −80° C. until analysis.

The study runs for two plus four weeks with the children consuming either placebo and/or treatment product daily. Compliance is monitored through the interactive internet enabled system.

The participants also use the system to record:
Bristol Stool Form Scale (BSFS) information
Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of period 1, faecal samples are collected and new treatment or placebo products are distributed. At the end of period 2 (exit visit), each children has a visit with the medical team and faecal samples are collected. After 6 months, faecal samples are collected at a follow up visit.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al., *Nucleic Acids Res.* 41, el (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries was measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

The faecal analyses reveals that HMOs are able to prevent antibiotic mitigated dysbiosis and enhance a favourable microbiota composition by increasing the abundance of bifidobacteria, preferably a *Bifidobacterium* within the *B. adolescentis* phylogenetic group and especially *Bifidobacterium adolescentis* and/or *B. pseudocatenulatum*, during and post antibiotic therapy. The children have reduced abundance of Proteobacteria and reduced levels of enterotoxigenic bacteria and their toxins, and reduced incidence of diarrhoea and abdominal pain.

Example 3

An in vitro intestinal system is used to simulate the colon region in a human infected with *C. difficile*. The reactors simulating the colon regions (proximal, transverse and distal) are inoculated with fresh faecal samples from a healthy individual age >65 years. After a stabilization and control period, antibiotics are dosed to the system to induce dysbiosis in the colon reactors. After cessation of antibiotic therapy, *C. difficile* spores are added to the colon reactors to develop *C. difficile* infection. Once a stable *C. difficile* infection is obtained treatment is initiated. Two different treatments (A and B) are run in parallel for 2 weeks. A: 2'-FL and LNnT (ratio 4:1) plus antibiotics for seven days and 2'-FL and LNnT (ratio 4:1) alone for the next seven days, B: antibiotics for seven days and no treatment for the next seven days. After the two weeks treatment period, the model is run as a follow up for two weeks to assess if infection will reoccur. At several time points (at the control, treatment and follow up period), the microbiota community and bacterial metabolites are measured using 16S sequencing and gas chromatography, respectively. Additionally, spores and viable *C. difficile* are measured.

The microbiota analysis reveals that HMOs are able to increase the level of bifidobacteria even in the presence of antibiotics and can change the microbiota community including their metabolites towards a more balanced profile after the antibiotic treatment has ceased. Additionally, the HMOs inhibit the spores and viable *C. difficile*, decreasing the reoccurrence of infection.

Example 4—Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (*Stevia*), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals and antioxidants, and meets FODMAP criteria. Further, the composition contains a mixture of one or more fucosylated HMOs and one or more core HMOs which are able to promote the growth of beneficial intestinal bacteria, modulate chronic inflammation, improve mucosal barrier integrity and reduce anxiety and depression.

Example 5—Capsule Composition

A capsule is prepared by filling about 2 g of a mixture of one or more fucosylated HMOs and one or more core HMOs into a 000 gelatine capsule using a filing machine. The capsules are then closed.

The invention claimed is:
1. A method of treating a disorder associated with antibiotic therapy comprising administering daily to a human in need thereof at least 2 g of a synthetic composition consisting essentially of one or more human milk oligosaccharides (HMOs) selected from the group consisting of fucosylated HMOs and core HMOs, and optionally, a probiotic,
wherein the disorder associated with antibiotic therapy is selected from the group consisting of diarrhoea, dysbiosis of the lower gastro-intestinal tract, and primary or recurrent *Clostridium difficile* infection, and wherein the human is undergoing or had previously undergone antibiotic therapy.
2. The method according to claim 1, wherein the fucosylated HMO is selected from the group consisting of 2'-FL, DFL and a mixture thereof; and the core HMO is selected from the group consisting of LNT, LNnT and a mixture thereof.
3. The method according to 1, wherein the one or more HMOs consists essentially of a mixture of one or more fucosylated HMOs and one or more core HMOs.
4. The method according to claim 3, wherein the mixture consists of 2'-FL and LNnT.
5. The method according to claim 3, wherein the mixture of one or more fucosylated HMOs and one or more core HMOs is in a ratio from about 1.5:1 to about 5:1 by weight.
6. The method according to claim 1, in which the one or more HMOs are administered neat, as diluted with water or in one or more unit dosage forms.
7. The method according to claim 1, wherein the amount of the one or more HMOs is from about 2 g to about 10 g.
8. The method according to claim 1, wherein the one or more HMOs is administered daily during the treatment period and for at least 14 days after termination of antibiotic therapy, or at least 14 days after termination of antibiotic therapy.
9. The method according to claim 1, wherein the human is a child of 3 years of age or older or an elderly person of 60 years of age or older.
10. The method according to claim 1, wherein the antibiotic therapy comprises a broad spectrum antibiotic.

* * * * *